United States Patent
Berg et al.

(10) Patent No.: US 6,391,036 B1
(45) Date of Patent: May 21, 2002

(54) MEDICAL GRAFT CONNECTOR OR PLUG STRUCTURES, AND METHODS OF MAKING AND INSTALLING SAME

(75) Inventors: Todd Allen Berg, Lino Lakes; Alex Alden Peterson, Maple Grove; Mark D. Wahlberg, St. Paul, all of MN (US)

(73) Assignee: St. Jude Medical ATG Inc., Maple Grove, MN (US)

( * ) Notice: Subject to any disclaimer, the term of this patent is extended or adjusted under 35 U.S.C. 154(b) by 0 days.

(21) Appl. No.: 09/540,665

(22) Filed: Mar. 31, 2000

Related U.S. Application Data

(62) Division of application No. 09/016,721, filed on Jan. 30, 1998, now abandoned.

(51) Int. Cl.$^7$ ............................................. A61B 17/08
(52) U.S. Cl. ..................... 606/151; 606/153; 606/155
(58) Field of Search .................. 606/151, 153, 606/155, 156; 411/502, 503, 508, 509, 510; 29/235, 237; 623/1.1, 23.64; 604/174; 128/898

(56) References Cited

U.S. PATENT DOCUMENTS

| | | | |
|---|---|---|---|
| 4,083,162 A | * 4/1978 | Regan et al. | ................ 411/508 |
| 4,214,587 A | 7/1980 | Sakura, Jr. | .............. 128/334 R |
| 4,503,569 A | 3/1985 | Dotter | ............................ 3/1.4 |
| 4,592,754 A | 6/1986 | Gupte et al. | .................... 623/1 |
| 4,617,932 A | 10/1986 | Kornberg | ................ 128/334 R |

(List continued on next page.)

FOREIGN PATENT DOCUMENTS

| | | | | |
|---|---|---|---|---|
| AU | 670239 | 1/1994 | ............. | A61F/2/06 |
| DE | OS 195 42 733 | 7/1997 | ........... | A61B/17/11 |
| EP | 539237 A1 | 4/1993 | ............. | A61F/2/06 |
| EP | 637 454 A1 | 2/1995 | ........... | A61M/25/10 |
| EP | 680 734 A2 | 11/1995 | ............. | A61F/2/06 |
| EP | 684 022 A2 | 11/1995 | ............. | A61F/2/06 |
| EP | 712 614 A1 | 5/1996 | ............. | A61F/2/06 |
| WO | WO 93/00868 | 1/1993 | ............. | A61F/2/06 |
| WO | WO 95/32757 | 12/1995 | ........... | A61M/29/00 |
| WO | WO 96/01591 | 1/1996 | ........... | A61B/17/22 |
| WO | WO 96/01599 | 1/1996 | ............. | A61F/2/06 |
| WO | WO 96/18361 | 6/1996 | ............. | A61F/2/06 |
| WO | WO 96/22745 | 8/1996 | ............. | A61F/2/06 |
| WO | WO 97/13463 | 4/1997 | ........... | A61B/17/00 |
| WO | WO 97/13471 | 4/1997 | ........... | A61B/19/00 |
| WO | WO 97/27898 | 8/1997 | ........... | A61M/29/00 |
| WO | WO 98/02099 | 1/1998 | ........... | A61B/17/00 |
| WO | WO 98/03118 | 1/1998 | ........... | A61B/17/11 |

*Primary Examiner*—David O. Reip
*Assistant Examiner*—Julian W. Woo
(74) *Attorney, Agent, or Firm*—Fish & Neave; Robert R. Jackson

(57) ABSTRACT

A medical graft connector or plug is made, for example, by cutting end portions of a tube of highly elastic material axially at numerous locations spaced circumferentially around the tube to produce a plurality of fingers which extend axially from each end of an uncut medial portion of the tube. The fingers are deflected radially outwardly from the medial portion and set in that condition. For a graft connector, the medial portion is coaxially connected to an end portion of a tubular graft. The connector is then installed through an aperture in the side wall of a patient's tubular body conduit, for example, by using a delivery tube in which the fingers are elastically deflected back to approximately their initial positions. When the delivery conduit is withdrawn from the connector, the fingers spring out to engage the inner and outer surfaces of the body conduit wall. For a plug, the medial portion is occluded and then the structure is installed through the aperture to be plugged in a manner similar to installation of the connector.

43 Claims, 8 Drawing Sheets

U.S. PATENT DOCUMENTS

| | | | |
|---|---|---|---|
| 4,665,906 A | 5/1987 | Jervis | 128/92 YN |
| 4,787,899 A | 11/1988 | Lazarus | 623/1 |
| 5,104,399 A | 4/1992 | Lazarus | 623/1 |
| 5,122,156 A | 6/1992 | Granger et al. | 606/219 |
| 5,135,467 A | 8/1992 | Citron | 600/16 |
| 5,211,658 A | 5/1993 | Clouse | 623/1 |
| 5,211,683 A | 5/1993 | Maginot | 128/898 |
| 5,234,447 A | 8/1993 | Kaster et al. | 606/153 |
| 5,275,622 A | 1/1994 | Lazarus et al. | 623/1 |
| 5,304,220 A | 4/1994 | Maginot | 623/1 |
| 5,316,023 A | 5/1994 | Palmaz et al. | 128/898 |
| 5,334,217 A | 8/1994 | Das | 606/213 |
| 5,354,336 A | 10/1994 | Kelman et al. | 623/6 |
| 5,387,235 A | 2/1995 | Chuter | 623/1 |
| 5,391,156 A * | 2/1995 | Hildwein et al. | 411/503 |
| 5,397,345 A | 3/1995 | Lazarus | 623/1 |
| 5,433,727 A | 7/1995 | Sideris | 606/213 |
| 5,443,497 A | 8/1995 | Venbrux | 623/1 |
| 5,452,733 A | 9/1995 | Sterman et al. | 128/898 |
| 5,456,712 A | 10/1995 | Maginot | 623/1 |
| 5,489,295 A | 2/1996 | Piplani et al. | 623/1 |
| 5,507,769 A | 4/1996 | Marin et al. | 606/198 |
| 5,522,880 A | 6/1996 | Barone et al. | 623/1 |
| 5,545,214 A | 8/1996 | Stevens | 623/2 |
| 5,562,728 A | 10/1996 | Lazarus et al. | 623/1 |
| 5,653,747 A | 8/1997 | Dereume | 623/1 |
| 5,676,670 A | 10/1997 | Kim | 606/108 |
| 5,695,504 A | 12/1997 | Gifford, III et al. | 606/153 |
| 5,976,178 A | 11/1999 | Goldsteen et al. | 623/1 |

\* cited by examiner

MEDICAL GRAFT CONNECTOR OR PLUG STRUCTURES, AND METHODS OF MAKING AND INSTALLING SAME

This is a division of U.S. patent application Ser. No. 09/016,721, filed Jan. 30, 1998, now abandoned, which is hereby incorporated by reference herein in its entirety.

BACKGROUND OF THE INVENTION

This invention relates to structures that can be used to make connections between tubular medical grafts and a patient's tubular body conduits. The structures of the invention can alternatively be constructed for use as medical plugs (e.g., to close atrial or ventricular septal defects). The invention also relates to methods for making and using the structures mentioned above.

Tubular grafts are frequently needed in medical procedures. For example, a coronary bypass procedure may involve the installation of a tubular graft between an aperture that has been formed in the side wall of the aorta and an aperture that has been formed in the side wall of a coronary artery downstream from an occlusion or blockage in that artery. Each end of the graft must be connected to the side wall of either the aorta or the coronary artery. Each such connection must extend annularly around the associated end of the graft conduit and be fluid-tight so that no blood will leak out. One common way to produce such connections is by suturing. It will be appreciated, however, that making such connections by suturing can be extremely difficult, time-consuming, and dependent on the skill of the physician for the quality of the results. There is also increasing interest in less invasive procedures which tend to impose constraints on the physician's access to the sites at which graft connections must be made and thereby make it more difficult or even impossible to use suturing to make such connections (see, for example, Goldsteen et al. U.S. Pat. No. 5,976,178, Sullivan et al. U.S. patent application Ser. No. 08/844,992, filed Apr. 23, 1997, and Sullivan et al. U.S. patent application Ser. No. 08/869,808, filed Jun. 5, 1997, all of which are hereby incorporated by reference herein in their entireties). Various types of mechanical connectors have been developed to reduce or eliminate the need for suturing, but improvements are constantly sought for such mechanical connectors with respect to considerations such as ease and speed of use, ease of manufacture, strength and permanence of the resulting connection, etc.

Plugs are also needed in a variety of medical procedures. For example, it may be necessary to plug an atrial or ventricular septal defect in the heart of a new-born child. Again, improvements are constantly sought for plugs which can be easily and quickly installed using minimally invasive procedures.

In view of the foregoing, it is an object of this invention to provide improved and simplified graft connectors.

It is another object of this invention to provide improved and simplified medical plugs.

It is still another object of this invention to provide improved and simplified methods of making structures that can be used as either medical graft connectors or plugs.

It is yet another object of this invention to provide improved and simplified methods for installing medical graft connectors or plugs.

SUMMARY OF THE INVENTION

These and other objects of the invention are accomplished in accordance with the principles of the invention by providing a connector or plug structure preferably formed by starting from a tube of highly elastic material such as nickel and titanium alloy (nitinol) metal. Each end portion of the tube is cut substantially axially at numerous locations spaced circumferentially around the tube to produce a plurality of fingers that extend substantially axially from each end of a remaining medial portion of the tube. The fingers at each end of the medial portion are then deflected so that they extend substantially radially out from the medial portion, and the fingers are set (e.g., by a heat treatment) in that deflected condition. For use of the structure as a graft connector, the medial portion is attached substantially coaxially to an end portion of a graft conduit. For use of the structure as a plug the medial portion of the tube is filled with a suitable plugging material or structure.

To install the graft connector or plug in a patient the fingers at each axial end of the medial portion may be elastically deformed back toward their initial condition (in which the fingers extend substantially axially from the ends of the medial portion). The structure may then be inserted in a delivery tube, which may maintain the fingers in their substantially axially extending condition. The delivery tube may then be inserted through the aperture in the side wall of the patient's tubular body conduit to which the end of the graft conduit is to be attached, or through the aperture in the patient's tissue structure that is to be plugged. The delivery conduit may then be removed from around the connector or plug structure. This releases the fingers at each end of the medial portion to spring out on respective opposite sides of the tissue structure to which the connection is to be made, or to which the plug is to be applied.

In some cases fingers may only be formed in one end of a starting tube. A connector may then be provided using two such tubes concentric with one another and with a graft conduit. In such an assembly the fingers on the two tubes extend from generally opposite axial ends of the assembly. Two such tubes may be similarly used to make a plug, although in this case the graft conduit is omitted and the interior of the structure is filled with a plugging material or structure.

As an alternative or addition to use of a delivery tube to releasably hold the fingers substantially parallel to the longitudinal axis of a connector or plug, another structure may be removably placed around the fingers. Examples of such another structure include a collar or a strand of material such as wire or suture material.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
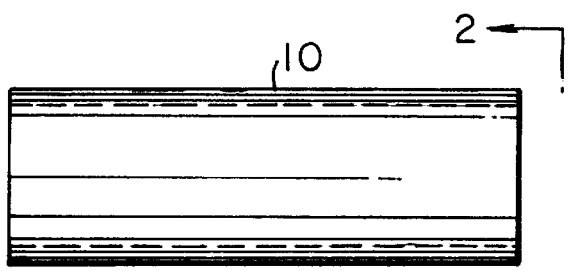
FIG. 1 is a side elevational view of an illustrative embodiment of a starting component for a structure of this invention.
Figure 2:
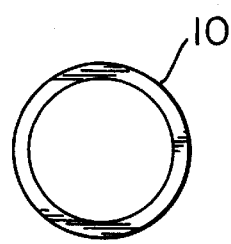
FIG. 2 is an end elevational view of the component of FIG. 1.

An illustrative starting component for the connector or plug structures of this invention is a hollow tube 10 as shown in FIGS. 1 and 2. Tube 10 may have any length, diameter, and wall thickness suitable for the intended use of the finished connector or plug structure. For use as a cardiac bypass graft connector, for example, tube 10 may have a diameter of about 4.0 millimeters, a wall thickness of about 0.003 inches, and a length of about 7.0 millimeters. It will be understood, however, that these specific dimensions are only exemplary, and that any other dimensions can be used instead if desired. The material of tube 10 is preferably highly elastic. A particularly preferred material is nickel titanium alloy (nitinol) metal (which can be per se conventional), but other materials such as stainless steel or thermoplastics can be used instead if desired.

Figure 3:
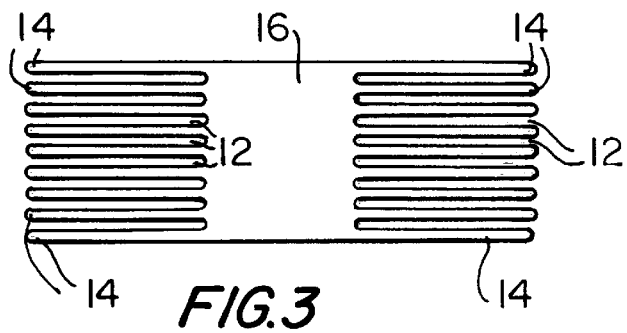
FIG. 3 is a side elevational view of the FIG. 1 component after some processing in accordance with the invention.

A first step in processing tube 10 in accordance with the invention is to cut into it substantially axially at many locations 12 spaced circumferentially around each axial end portion as shown in FIG. 3. Cuts 12 reduce starting tube 10 to a plurality of fingers 14 extending substantially axially from each end of an uncut medial tube portion 16. Cuts 12 may be made by any suitable technique such as electron discharge machining ("EDM"), laser cutting, or etching. The length of medial portion 16 may be selected based on the intended use of the structure. For example, the length of medial portion 16 may be selected to correspond to the thickness of the patient's body tissue through which the medial portion will extend. Illustrative lengths for medial portion 16 are in the range from about 0.2 millimeters to about 4.0 millimeters. The length of fingers 14 may also be selected based on the intended use of the structure. Illustrative lengths for fingers 14 are in the range from about 1.0 millimeter to about 10.0 millimeters.

Figure 4:
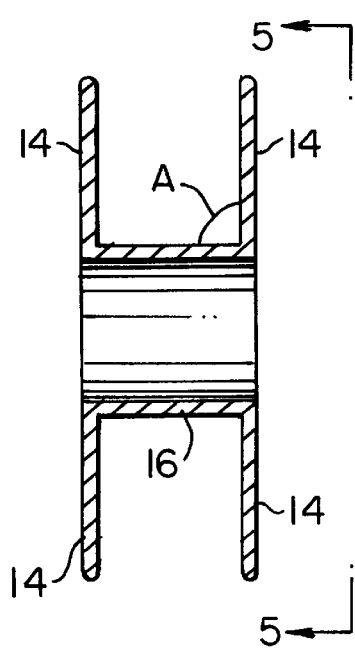
FIG. 4 is a sectional view of the FIG. 3 component after further processing in accordance with the invention.
Figure 5:
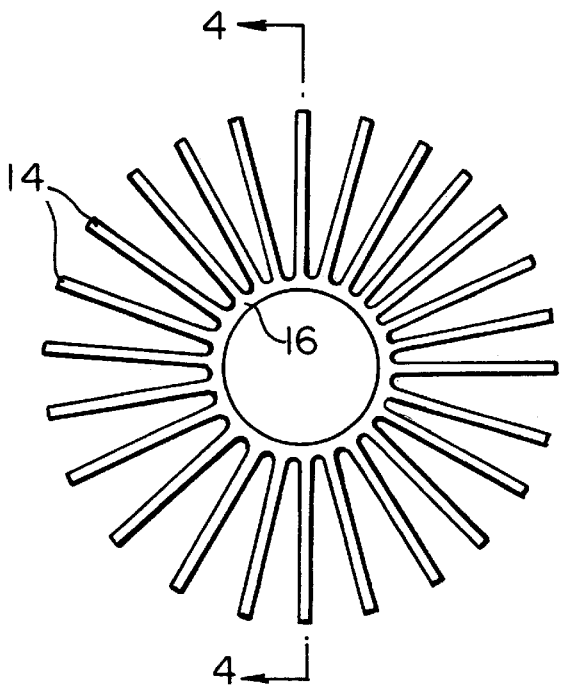
FIG. 5 is an end elevational view of the FIG. 4 component.
Figure 6:
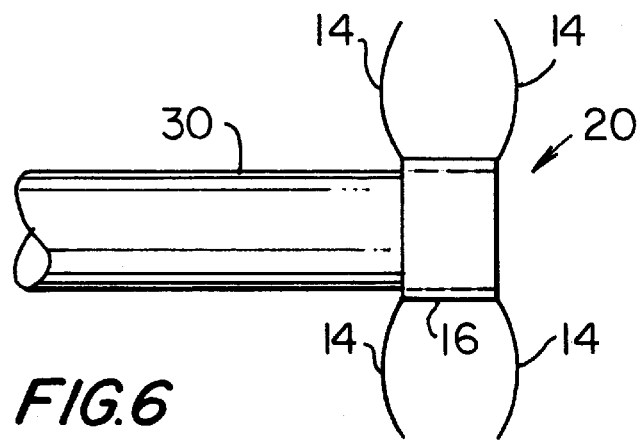
FIG. 6 is a simplified side elevational view of the FIG. 4 component with a graft conduit added so that the FIG. 4 component can be used as a connector for the graft conduit.
Figure 17:
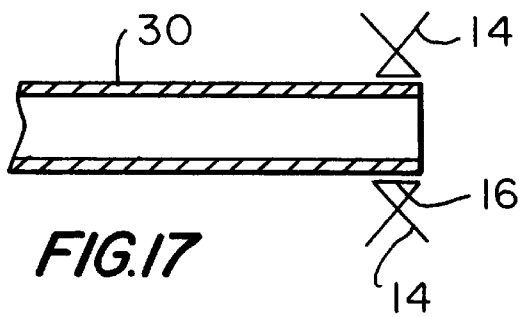
FIG. 17 is a simplified sectional view showing an assembly similar to the assembly shown in FIG. 6, but with an illustrative modification in accordance with the invention.

The next step is to deflect fingers 14 to approximately the positions that it is desired for them to have in the finished and installed connector or plug structure. For example, FIGS. 4 and 5 show deflecting fingers 14 substantially radially out from the end of medial portion 16 that each finger is attached to. Although FIGS. 4 and 5 show the angle A between each finger 14 and the adjacent axially extending surface of medial portion 16 as approximately 90°, it will be understood that a wide range of angles A (e.g., in the range from about 45° to about 120°) can be used. Indeed, the angle of deflection of various fingers 14 can be different if desired. In addition, fingers 14 can be curved (e.g., concave curved as viewed from a plane extending radially out from medial portion 16) rather than straight if desired, and indeed outward curvature of the fingers can be used in place of outward deflection by a definite angle A. For example, the free ends of the fingers 14 at one or both ends can curve toward or even overlap the free ends of the fingers at the other end. FIG. 6 and some subsequent FIGS. show examples of such curvature of fingers 14. FIG. 17 shows an example of overlapping fingers 14. In general, however, fingers 14 will be deflected so that they have at least a component of radially outward extension from medial portion 16. For convenience and simplicity herein it will therefore sometimes be said that fingers 14 extend radially out from medial portion 16, even though it will be understood that this wording includes (1) fingers having only a component of such radially outward extension, and (2) fingers that are either substantially straight or curved.

It will also be appreciated that it may be desirable to deflect fingers 14 beyond their desired final positions so that when they are subsequently released during deployment, they will resiliently bear on the tissue in which the connector or plug is installed in their effort to return to the positions to which they have been deflected in this step of their manufacture. For example, if FIG. 4 shows the desired final position of fingers 14 in use in a patient (i.e., angle A=90°), it might be desirable at this stage in the manufacturing process to deflect fingers 14 more than is shown in FIG. 4 (e.g., to angle A=60°) to increase the security with which fingers 14 will engage tissue surrounding medial portion 16. Nevertheless, for convenience and simplicity herein it will sometimes be said that in this manufacturing step fingers 14 are deflected to (or at least to) approximately their intended final positions, it being understood that this wording includes deflecting fingers beyond the actual intended final positions.

When fingers 14 have been deflected to approximately their final intended positions (e.g., as shown in FIGS. 4 and 5), fingers 14 are set in those positions. For example, a heat treatment may be applied to the structure to set fingers 14 in their deflected positions.

Figure 7:
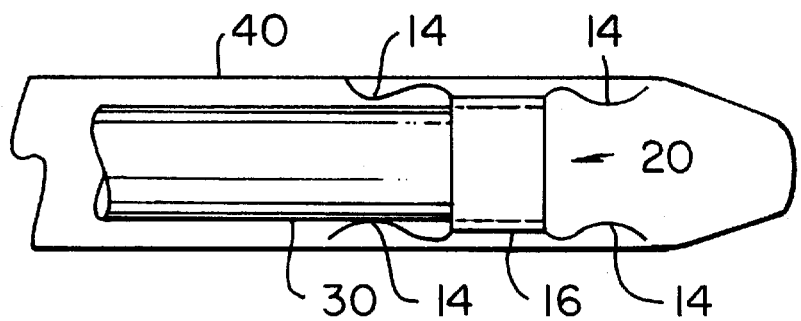
FIG. 7 is a simplified, partly cut away, side elevational view of the FIG. 6 assembly in illustrative apparatus for use in installing the FIG. 6 assembly in a patient.
Figure 8:
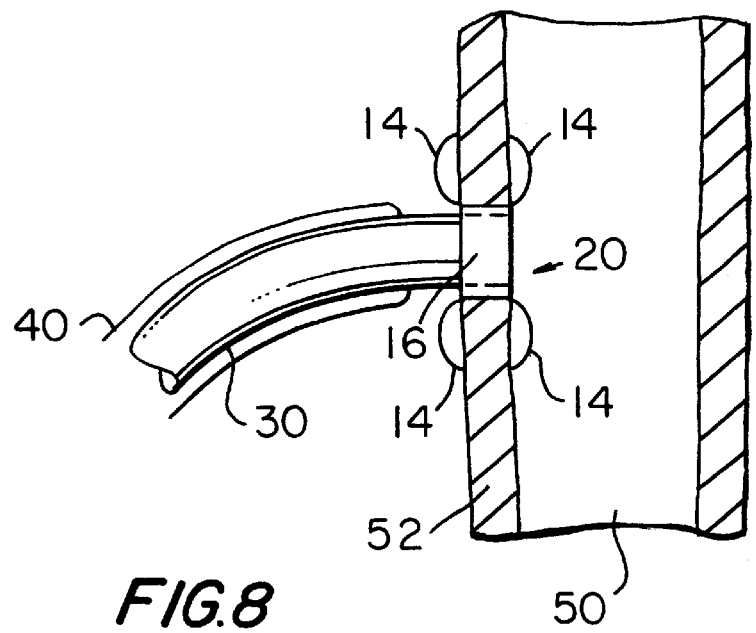
FIG. 8 illustrates use of the FIG. 7 apparatus to install the FIG. 6 assembly in a patient.

FIGS. 6–8 show use of a structure of the type shown in FIGS. 4 and 5 to provide a connector 20 for an end of graft conduit 30. (The possible alternative use of structures of the type shown in FIGS. 4 and 5 as a plug rather than a graft connector will be discussed after explanation of the connector embodiment is substantially complete.) Graft conduit 30 may be natural conduit (e.g., a relocated portion of the patient's tubular body tissue), artificial conduit (e.g., of the type shown in above-mentioned U.S. Pat. No. 5,976,178), or a composite of natural and artificial conduits.

In the illustrative embodiment shown in FIG. 6 an axial end portion of graft conduit 30 is inserted substantially coaxially into and attached to medial portion 16. Depending on the materials of components 20 and 30, they may be secured together by any suitable means such as suturing, adhesive, welding, etc.

The next step in use of the graft 30 and connector 20 is to insert that assembly into a delivery tube 40 as shown in FIG. 7. Tube 40 is preferably slightly larger in diameter than medial portion 16 or graft conduit 30. To fit structure 20 into tube 40 fingers 14 are resiliently deflected back toward their initial positions as axial extensions from the ends of medial portion 16 as shown in FIG. 7. In other words, fingers 14 are elastically deflected inwardly toward parallelism with a central longitudinal axis of medial portion 16. If connector 20 is made of nitinol, temporary super-cooling of the connector may be used at this stage to facilitate assembly of components 20 and 30 in delivery tube 40 (assuming that graft conduit 30 can tolerate proximity to super-cooled connector 20). Super-cooling nitinol makes it very plastic so that fingers 14 can be straightened out and so that they will hold that shape for insertion of components 20 and 30 into tube 40. When connector 20 warms up again, it "remembers" the shape it was given during the step in which the fingers were set after being radially outwardly deflected.

The next step in use of the assembly shown in FIG. 7 is to insert delivery tube 40 through an aperture in the side wall of the patient's tubular body conduit (50 in FIG. 8) to which graft conduit 30 is to be connected by connector 20. For example, a tapered distal end portion of delivery tube 40 (shown on the right in FIG. 7) may be used to help tube 40 enter the aperture in tubular body conduit side wall 52. Elements 20, 30, and 40 are preferably positioned relative to side wall 52 so that medial portion 16 is approximately centered on side wall 52. This places the fingers 14 at one axial end of medial portion 16 inside conduit 50, while the fingers 14 at the other end of medial portion 16 are outside conduit 50.

The next step is illustrated by FIG. 8 and involves the withdrawal of delivery tube 40 from the aperture in side wall 52, while components 20 and 30 are held stationary relative to side wall 52. As delivery tube 40 is thus withdrawn, the fingers 14 on the inside of conduit 50 are gradually released to resiliently spring out inside side wall 52 around the aperture through that wall. Thereafter, as delivery tube 40 continues to be retracted, the finger 14 on the outside of conduit 50 are also released to resiliently spring out outside side wall 52 around the aperture through that wall. Thus the final condition of connector 20 is as shown in FIG. 8 (although of course delivery tube 40 is ultimately completely withdrawn from the patient). The fingers 14 on the inside of conduit 50 prevent the connector and graft conduit from pulling out of the aperture in side wall 52. The fingers 14 on the outside of conduit 50 prevent the connector and graft conduit from protruding undesirably far into conduit 50.

Although FIGS. 7 and 8 show inserting connector 20 into the aperture in the side wall 52 of conduit 50 from outside that conduit, connector 20 could alternatively be inserted from inside the lumen of conduit 50. In that case connector 20 would typically be located at a medial position in delivery tube 40, with graft conduit 30 extending from the connector in the distal direction along the interior of tube 40. Tube 40 would then be inserted intraluminally into conduit 50 until the location of the aperture in wall 52 is reached. Tube 40 would then be passed out of the aperture in wall 52 until medial portion 16 is centered on wall 52. Components 20 and 30 would then be held stationary relative to conduit 50 while tube 40 is pulled back proximally via the lumen of conduit 50, thereby exposing graft conduit 30 outside conduit 50 and similarly exposing connector 20 so that fingers 14 can spring out and engage the inner and outer surfaces of side wall 52 around the aperture in that side wall. A separate axially extending pusher or holder structure may be needed inside tube 40 to help hold components 20 and 30 stationary as described above while tube 40 is pulled back proximally.

Figure 9:
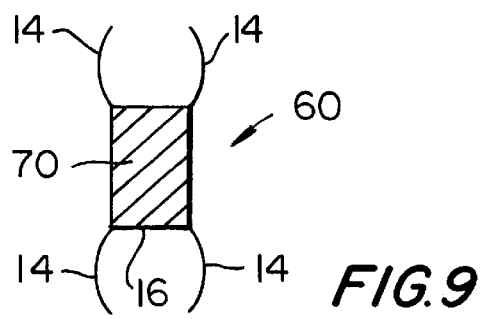
FIG. 9 is a simplified sectional view of the FIG. 4 component with plug material or structure added so that the FIG. 4 component can be used as a plug.
Figure 10:
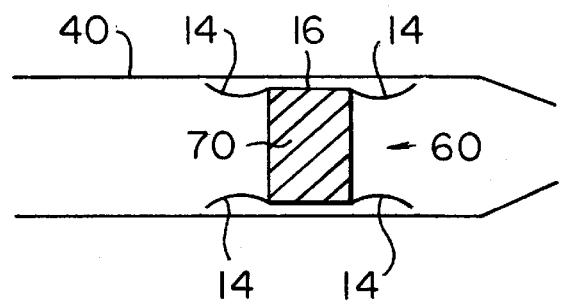
FIG. 10 is a view similar to FIG. 7, but for the plug embodiment of FIG. 9.

FIG. 9 shows an alternative embodiment in which a structure of the type shown in FIGS. 4 and 5 is adapted for use as a plug 60. In this alternative medial portion 16 is substantially filled or occluded with a plug material or structure 70 such as silicone or thermoplastic. Plug 60 is then inserted in a delivery tube 40 as shown in FIG. 10 in substantially the same way that tube 40 is used with component 20 in FIG. 7.

Figure 11:
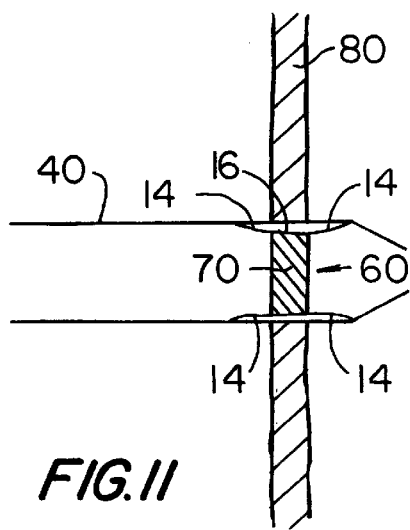
FIG. 11 is a view somewhat like FIG. 8, but for the plug embodiment of FIGS. 9 and 10.

The next step in the use of assembly 40/60 is to insert tube 40 through the aperture in the tissue structure 80 that is to be plugged as shown in FIG. 11. As in the previously described connector embodiment, assembly 40/60 is preferably positioned relative to tissue structure 80 so that the fingers 14 extending from one axial end of medial portion 16 are on one side of structure 80, and so that the fingers 14 extending from the other axial end of medial portion 16 are on the other side of structure 80.

Figure 12:
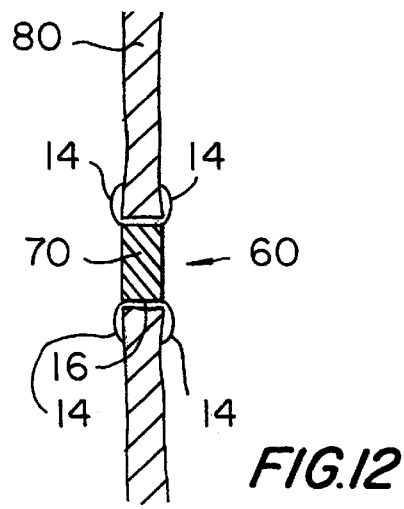
FIG. 12 is another view somewhat like FIG. 11, but showing a fully installed plug of the type shown in FIG. 9.

The next step is to withdraw tube 40 from the aperture in tissue structure 80, while holding plug 60 substantially stationary relative to structure 80. To hold plug 60 stationary in this manner, a holder tube (not shown) may be inserted into tube 40 until the distal end of the holder tube bears on plug structure 70. Then the holder tube can be held stationary relative to tissue structure 80 while tube 40 is withdrawn. As tube 40 is withdrawn, the fingers 14 on the right-hand side of structure 80 as viewed in FIGS. 11 and 12 are gradually released to spring resiliently out against that side of structure 80. Further withdrawal of tube 40 allows the fingers on the left-hand side of structure 80 to spring resiliently out against that side of structure 80. The completed plug installation is as shown in FIG. 12.

As in the case of connector 20, plug 60 can be inserted into the aperture in tissue structure 80 from either side of that tissue structure, and tube 40 can similarly be withdrawn in either direction. For example, if tissue structure 80 is the wall of a conduit or chamber, plug 60 can be installed from either the inside or outside of that conduit or chamber, and tube 40 can be withdrawn via either the inside or outside of that conduit or chamber.

Manufacture of the connector or plug structures described above is greatly facilitated by the fact that elements 14 and 16 all come from one starting structure (i.e., tube 10). Elements 14 and 16 are therefore integral at all times, and there is no need to attempt to assemble relatively small fingers 14 on another component. Use of the connector or plug structures of this invention is extremely easy because all that is required is to properly position the connector or plug relative to the appropriate tissue of the patient and then withdraw the delivery tube 40 from around the connector or plug. Fingers 14 automatically spring out into the positions required to complete and secure the connector or plug.

Figure 13:
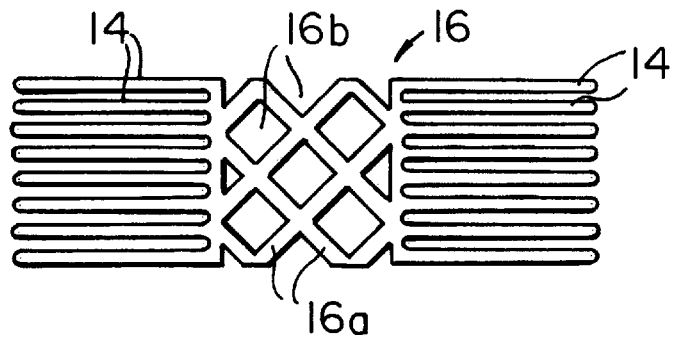
FIG. 13 is another view similar to FIG. 3 showing an illustrative modification of a FIG. 3 type structure in accordance with the invention.

If desired, medial portion 16 can be perforated at any suitable time during the course of manufacturing a connector or plug in accordance with this invention. For example, FIG. 13 shows many perforations 16b in medial portion 16, thereby effectively reducing the medial portion to an open mesh of members 16a. Such perforation of medial portion 16 may increase its flexibility (e.g., axially and radially) and therefore its long-term acceptability in the patient's body. The radial compliance of a flexible connector or plug (i.e. the ability of such a structure to resiliently increase or decrease in circumference) is believed to be beneficial with respect to long-term body circuit lumen patency. Increased flexibility and radial compliance of medial portion 16 may also facilitate delivery and/or installation of the connector or plug. For example, flexibility of medial portion 16 may allow a connector or plug to be resiliently circumferentially compressed to a relatively small size to facilitate delivery of the connector or plug to an installation site (e.g., delivery through the lumen of a patient's body conduit). After the connector or plug has been delivered to the desired site in the patient's body in its circumferentially compressed size, the connector or plug is released from the delivery apparatus so that it can automatically return to its original larger size. In the case of a connector for a natural tissue graft, perforation of medial portion 16 may allow the tissue of the graft and conduit to which the graft is connected to grow together through the perforations.

Perforation of medial portion 16 may also allow that portion of a connector or plug to exert resilient, radially outward force on surrounding tissue on a long-term basis after the connector or plug has been installed. This may be useful for such purposes as firmer engagement of the surrounding tissue, reduced potential for fluid leakage around the connector or plug, etc. For example, if the elastic recoil of the surrounding tissue diminishes over time or if the tissue is relatively non-elastic due to disease or age, sealing between the tissue and the connector or plug may be reduced. In such cases, resilient outward expansion of the connector or plug can be helpful in compensating for deficiencies of the tissue. A connector or plug with a perforated medial portion 16 can resiliently expand to fill any opening that may otherwise tend to develop between portion 16 and the surrounding tissue if and when the elastic recoil of the tissue diminishes.

Whereas the depicted connector and plug embodiments are round, other shapes (e.g., ellipses, polygons, etc.) are equally possible. Similarly, the ends of medial portion 16 do not have to be perpendicular to the longitudinal axis of the connector or plug structure. Particularly in the case of connectors, it may be desired to have one or both ends of medial portion 16 skewed relative to the longitudinal axis of the connector (i.e., so that the longitudinal axis is not perpendicular to a plane defined by the skewed end of medial portion 16). The free ends of the adjacent fingers 14 may then be similarly skewed. Such skewing of portions of the connector may facilitate connecting the end of a graft to the side wall of a patient's body conduit at an angle other than 90° to that side wall. These and other illustrative examples of modifications, alternatives, and enhancements in accordance with the invention will now be discussed in more detail with reference to FIGS. 14–28.

Figure 14:
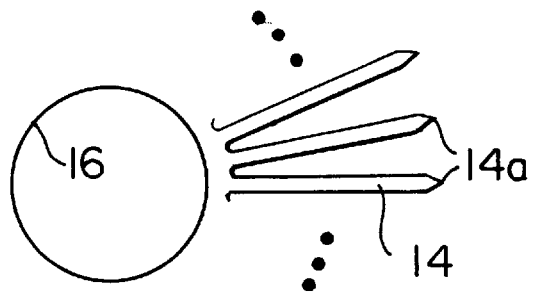
FIG. 14 is another view similar to a portion of FIG. 4 showing an illustrative modification of a FIG. 4 type structure in accordance with the invention.

FIG. 14 shows that the free ends of fingers 14 can be sharply pointed as indicated at 14a to facilitate engagement and or penetration of tissue by the fingers. This can be done, for example, by sharpening the associated axial end of the starting tube 10 to a sharp annular edge prior to making cuts 12 as shown in FIG. 3.

Figure 15:
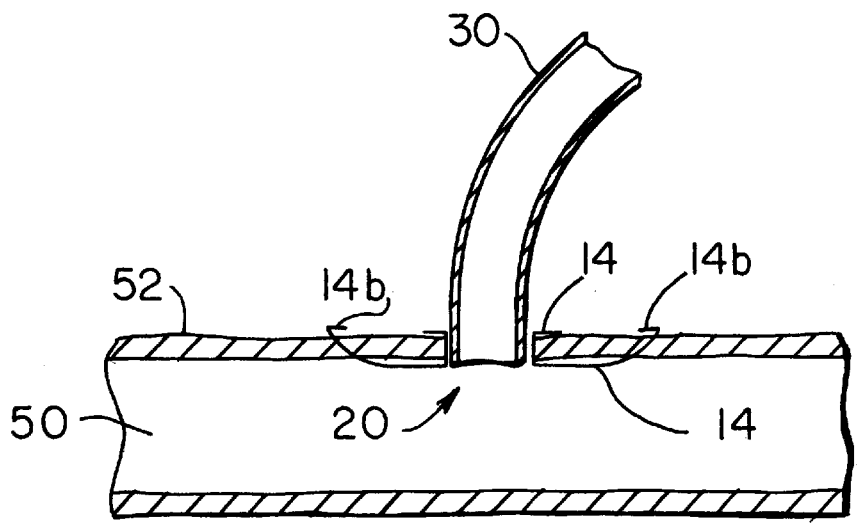
FIG. 15 is a sectional view somewhat like FIG. 8 showing illustrative modifications in accordance with the invention.

FIG. 15 shows the free ends of the fingers 14 that are generally on the inside of conduit 50 penetrating and passing through the conduit wall 52 to more firmly secure connector 20 to conduit 50. In addition, FIG. 15 shows that the free ends of the above-mentioned fingers 14 may be provided with barbs 14b (somewhat like the barbs on fishing hooks) that strongly resist withdrawal of the fingers after the fingers have penetrated the tissue of conduit wall 52. FIG. 15 still further shows that the fingers 14 on the inside of conduit 50 in a finished connection may be different from the fingers 14 on the outside of conduit 50. For example, the fingers 14 on the inside of conduit 50 may be longer, curved and sharply pointed for tissue penetration, and barbed as at 14b, while the fingers 14 on the outside of conduit 50 may be shorter, straighter, blunter, not barbed, and therefore not as adapted for tissue penetration. Such differences between the inner and outer fingers 14 may reflect different performance characteristics needed of them. Fluid pressure inside conduits 30 and 50 may attempt to force conduit 30 away from conduit 50, thereby necessitating relatively strong inner fingers 14. Concomitantly, there may be little tendency of conduit 30 to extend farther into conduit 50, so that outer fingers 14 can be relatively weak. Other differences that can be made between inner and outer fingers 14 include differences in number, spacing, width, etc.

Figure 16:
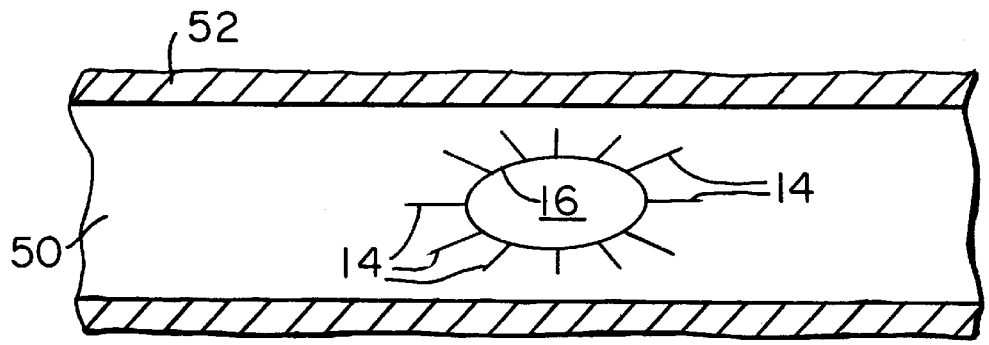
FIG. 16 is a simplified sectional view showing still other illustrative modifications in accordance with the invention.

FIG. 16 illustrates a point made earlier; namely, that a connector or plug in accordance with this invention can have a cross sectional shape other than round. In the particular example shown in FIG. 16 the connector or plug has an elliptical cross section, with the major axis of the ellipse substantially aligned with the longitudinal axis of conduit 50. In addition, FIG. 16 shows that different fingers 14 at either or both axial ends of medial portion 16 can have different lengths. In the particular example shown in FIG. 16 the fingers 14 that are more nearly aligned with the longitudinal axis of conduit 50 are longer than the fingers that are more nearly perpendicular to the longitudinal axis of conduit 50. To produce fingers 14 of different lengths, one or both axial ends of the starting tube 10 can be appropriately shaped prior to making cuts 12, or the free ends of the fingers can be trimmed after cuts 12 have been made.

FIG. 17 illustrates another possibility mentioned earlier; namely, that the fingers 14 extending from axially opposite ends of medial portion 16 may be deflected and set so that their free ends overlap. When a connector or plug made in this way is installed in a patient, this construction of fingers 14 helps to increase the contact area between fingers 14 and the tissue between them, as well as compression of the tissue between the fingers.

Figure 18:
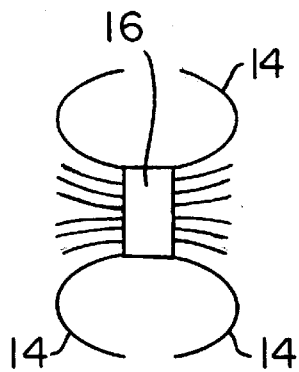
FIG. 18 is a simplified sectional view somewhat like FIG. 4 which is useful in explaining an illustrative modification in accordance with this invention.
Figure 19:
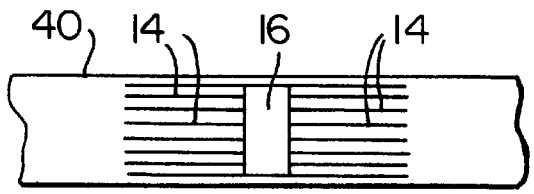
FIG. 19 is a view somewhat like FIG. 7 or FIG. 10 for the modified structure of FIG. 18.

It may desirable to make fingers 14 so that their flexural stiffness (especially in directions radial of medial portion 16) varies in a predetermined way along the length of each finger. This feature can be used, for example, to cause the fingers to assume a more nearly cylindrical shape when they are deflected for insertion into a delivery tube 40. Thus FIG. 18 shows a connector or plug which makes use of this possible feature prior to insertion into a delivery tube, and FIG. 19 shows the FIG. 18 structure after insertion into delivery tube 40. A comparison of FIGS. 7 or 10, on the one hand, with FIG. 19, on the other hand, reveals that in FIG. 19 fingers 14 form a more nearly cylindrical array at each axial end of medial portion 16 because the flexural stiffness of the fingers in FIGS. 18 and 19 has been tailored to produce this result.

Figure 20:
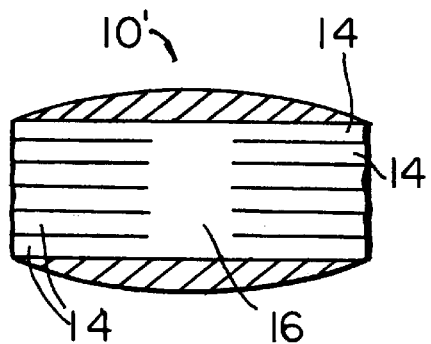
FIG. 20 is a simplified sectional view showing an illustrative precursor structure for embodiments of the type illustrated by FIGS. 18 and 19.
Figure 21:
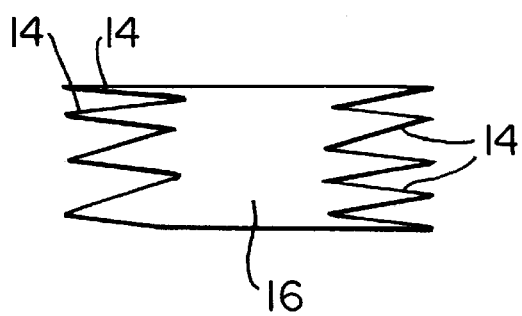
FIG. 21 is a simplified elevational view showing another illustrative precursor structure for embodiments of the type illustrated by FIGS. 18 and 19.

FIGS. 20 and 21 show illustrative techniques for tailoring the flexural stiffness of fingers 14 along their length as mentioned above in connection with FIGS. 18 and 19. In FIG. 20 the thickness of the wall of the starting tube 10' is varied along the length of the tube to give fingers 14 correspondingly varied thickness along their lengths. In FIG. 21 fingers 14 are cut so that their width varies along their length. If desired both techniques (FIG. 20 and FIG. 21) can be combined. In general terms, the geometry of fingers 14 can be tailored in any suitable way to cause fingers 14 to exhibit any desired elastic behavior.

Figure 22:
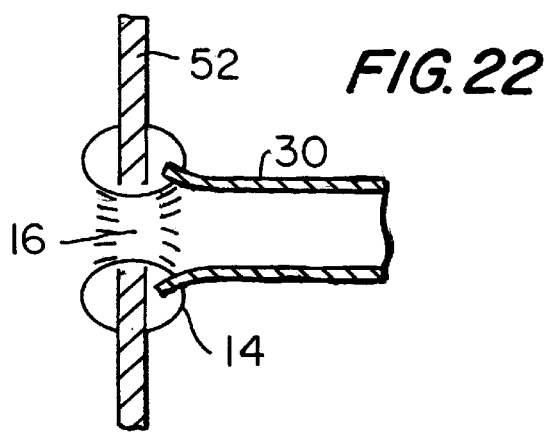
FIG. 22 is a simplified sectional view similar to FIG. 15 showing other illustrative modifications in accordance with the invention.

FIG. 22 illustrates another technique for attaching natural or artificial graft conduit 30 to a connector in accordance with this invention. As shown in FIG. 22 the fingers 14 at one end of medial portion 16 are made to pass through (e.g., by piercing) an annular end portion of graft conduit 30. When the connector and graft are installed in the patient through an aperture in the patient's body tissue wall 52, these fingers 14 curve back to contact one surface of wall 52, while the fingers 14 at the other end of medial portion 16 curve back to contact the other surface of wall 52.

Figure 23:
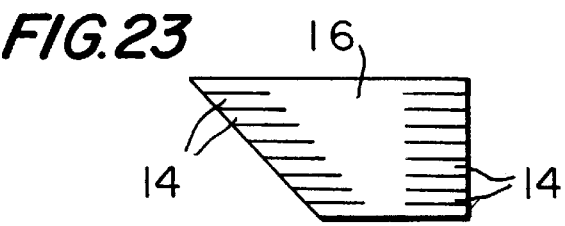
FIG. 23 is a simplified elevational view similar to FIG. 3 showing more illustrative modifications in accordance with the invention.

FIG. 23 illustrates another point that has already been mentioned briefly; namely, that an end of a connector of this invention can have an angle other than 90° to the longitudinal axis of the connector. In the example shown in FIG. 23 the left-hand end of the connector is not perpendicular to the longitudinal axis of the connector. This type of connector may be particularly suitable for connecting a graft conduit to the sidewall of another conduit at an angle which is not perpendicular to the longitudinal axis of the other conduit.

Figure 24:
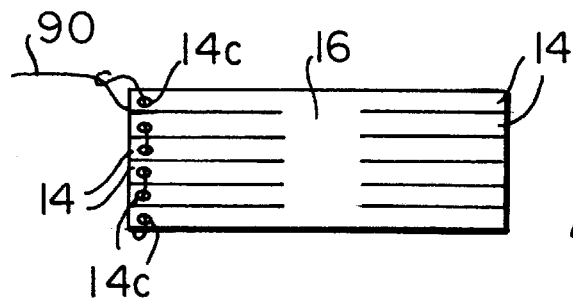
FIG. 24 is another simplified elevational view similar to FIG. 3 showing still more illustrative modifications in accordance with the invention.

FIG. 24 illustrates a technique that may be used to releasably hold fingers 14 in a desired configuration prior to deployment of a connector or plug in a patient. In this embodiment the free end portion of each finger 14 near one end of the connector or plug has a hole 14c through it. A wire 90 or other suitable material strand is threaded through these holes and formed into a loop that holds the fingers in a desired condition (in this case, a substantially cylindrical extension of medial portion 16). When loop 90 is undone and pulled out of holes 14c, the associated fingers 14 are released to spring radially out (e.g., as shown in FIG. 8 or FIG. 12). This type of releasable retention of fingers 14 can be used in place of or in addition to retention inside a delivery tube (e.g., tube 40 in FIG. 7 or 10) to facilitate control of the associated fingers until it is desired to fully deploy them. For example, such releasable confinement and control of fingers 14 may be useful to facilitate intraluminal delivery and deployment of a connector or plug.

Figure 25:
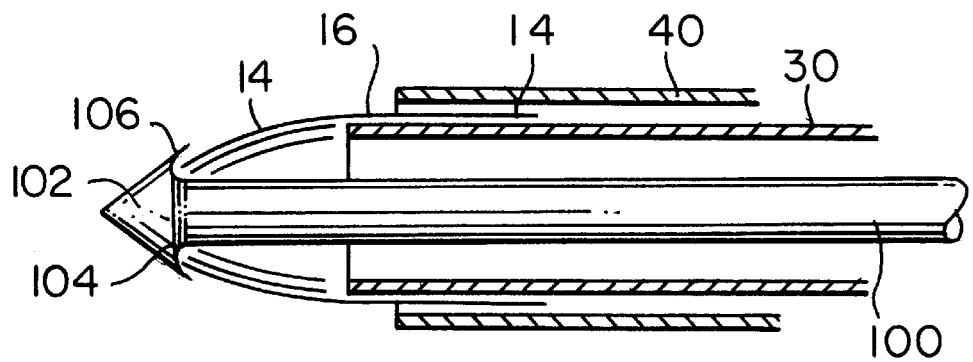
FIG. 25 is a simplified sectional view showing an illustrative alternative to apparatus of the type shown in FIG. 7.

FIG. 25 shows another example of a structure 100 for releasably confining fingers 14 on a connector. In this case structure 100 is an elongated tube or rod which extends axially through the connector. A somewhat enlarged head 102 on one end of structure 100 includes a recess 104 for releasably receiving the free ends of the fingers 14 at one end of medial portion 16. In other words, recess 104 defines a collar 106 that extends annularly around the adjacent free ends of fingers 14. When fingers 14 are thus received in recess 104 or collar 106, they are prevented from springing radially outwardly. However, when fingers 14 are released from recess 104 or collar 106 (e.g., by shifting structure 100 to the left relative to the other elements shown in FIG. 25), the fingers are free to resiliently spring radially outwardly. Structure 100 can then be removed (e.g., by pulling it back to the right as viewed in FIG. 25). Head 102 may additionally be sharply pointed as shown in FIG. 25 to act as an incisor and/or dilator for helping the structure to pass through a patient's body tissue wall prior to release of fingers 14 from recess 104 or collar 106. Structure 100 may be adapted for passage into a patient along a guide wire previously installed in the patient. For example, structure 100 may have a central, axially extending bore or lumen through which such a guide wire may pass. A central, axially extending guide structure may similarly be used with embodiments like the one shown in FIG. 7.

Figure 26:
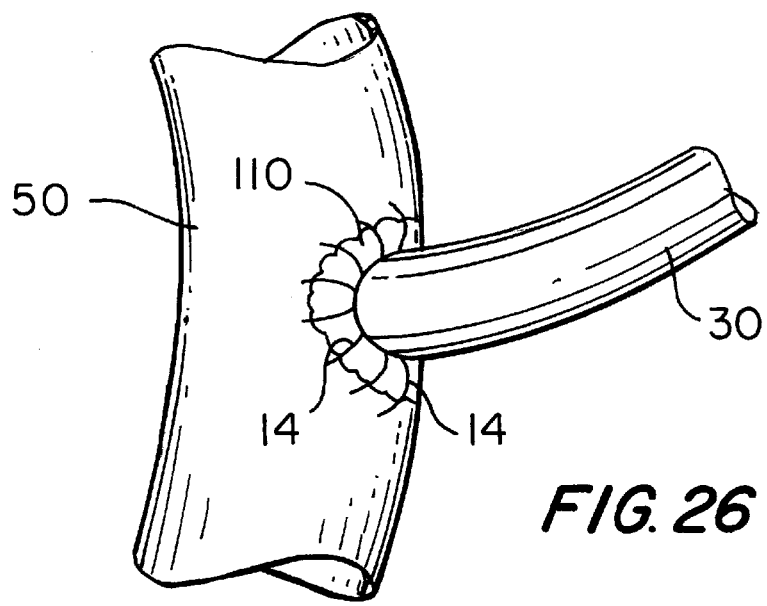
FIG. 26 is a simplified elevational view illustrating another possible modification of structures in accordance with the invention.

FIG. 26 shows possible modification of a connector in accordance with the invention to include a web 110 of a highly elastic material such as silicone between adjacent fingers 14. Such a web 110 can be provided on the fingers 14 at either or both ends of medial portion 16. Possible benefits of web 110 include enhanced sealing and faster clotting. If desired, a clot-enhancing or clot-promoting material or drug can be added to web 110.

Although not always specifically mentioned above, it will be understood that many of the features shown in FIGS. 14–26 are applicable to plugs as well as to graft connectors.

Figure 27:
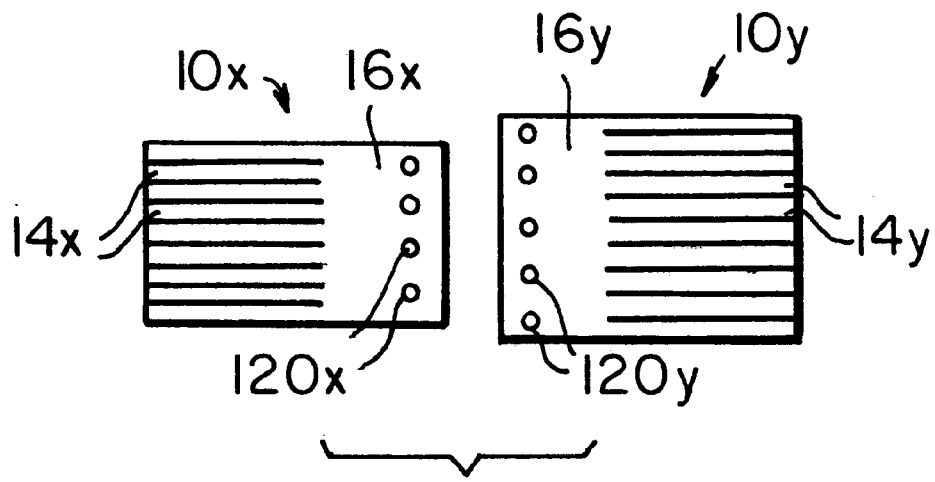
FIG. 27 is a simplified elevational view somewhat like FIG. 3 showing another illustrative embodiment of the invention.
Figure 28:
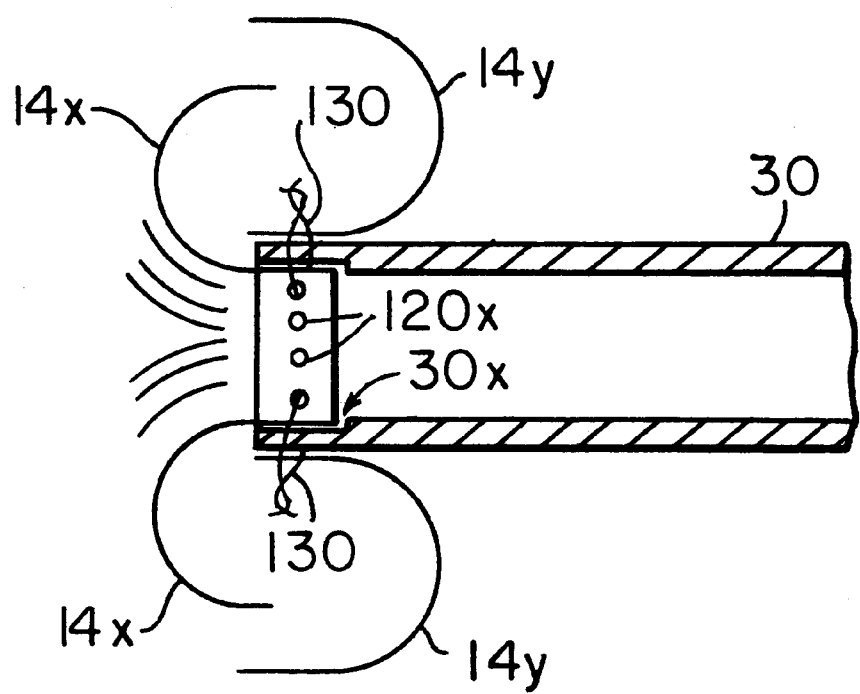
FIG. 28 is a simplified sectional view illustrating use of apparatus of the type shown in FIG. 27.

FIGS. 27 and 28 show an alternative embodiment in which a connector is assembled from two initially separate parts 10x and 10y. Each of parts 10x and 10y is preferably formed from a tube similar to the tube shown in FIGS. 1 and 2. The diameter of the tube used to form part 10y is somewhat larger than the diameter of the tube used to form part 10x. Fingers 14x and 14y are formed in one axial end portion of each tube. Holes 120x and 120y are formed in the other axial end portion of each tube. A medial portion 16x and 16y remains in each tube between the fingers 14 and the holes 120 of that tube. The fingers 14 on each tube are treated as described above for other embodiments (i.e., the fingers are deflected radially out and set in that condition).

Structures 10x and 10y are then assembled on an end of a graft conduit 30 as shown in FIG. 28. In particular, the perforated and medial portions of structure 10y are placed substantially concentrically around the outside of graft conduit 30, while structure 10x is placed substantially concentrically inside the graft conduit. Structures 10x and 10y are oriented so that their fingers 14 are oppositely directed along the longitudinal axis of graft conduit 30. Structures 10x, 10y, and 30 are secured together (e.g., by sutures 130 through radially adjacent holes 120x and 120y and the intervening wall material of conduit 30). As an alternative or addition to suturing, structures 10x, 10y, and 30 may be press fit together, and/or an adhesive may be used to help hold these components together. Fingers 14 may be resiliently deflected substantially parallel to the longitudinal axis of conduit 30 and away from the region of holes 120 if that will facilitate assembly of structures 10x and 10y on conduit 30. The assembly of structures 10x, 10y, and 30 may be delivered to and installed at a graft site in a patient in the same manner as is described above for any of the other connector embodiments.

Connectors of the type shown in FIGS. 27 and 28 may have the advantage that, even though one component 10x is inside conduit 30, that component can be radially recessed into conduit 30 as indicated at 30x, thereby leaving a substantially smooth passageway for fluid flow through conduit 30 and the connector. Such a smooth passageway is desirable for such purposes as avoiding any obstruction or disturbance (e.g., by causing turbulence) of the fluid flow. The recessing at 30x can be produced by clamping the tissue between the tubular portions of components 10x and 10y.

In some applications it might be possible to use only one structure like 10x or 10y in a graft connector. For example, it might be possible to eliminate structure 10y from FIG. 28. In addition, if structure 10y is eliminated from FIG. 28, the assembly shown in FIG. 28 could be further modified by placing structure 10x outside rather than inside the end of graft conduit 30. Any of the modifications and/or enhancements described above for other connector embodiments can also be applied to connectors of the type shown in FIGS. 27 and 28.

Structures of the type shown in FIGS. 27 and 28 are also usable to make plugs in accordance with this invention. For example, a structure like 10x may be assembled with a structure like 10y generally as shown in FIG. 28, but without graft conduit 30. The interior of the assembly would be occluded by a plugging material or structure, generally as shown at 70 in FIG. 9, to produce a completed plug. Such a plug would be installed as described above for any of the other plug embodiments.

It will be understood that the foregoing is only illustrative of the principles of the invention, and that still other modifications can be made by those skilled in the art without departing from the scope and spirit of the invention. For example, the various materials and dimensions mentioned herein are only examples, and other materials and dimensions can be used if desired. As another example of modifications within the scope of the invention, as an alternative to starting with a tube like tube 10 in FIGS. 1 and 2, one could start with a web of any material that would be suitable for tube 10. Two opposite marginal portions of the web would then be cut at numerous substantially parallel locations (somewhat like cuts 12 in FIG. 3), leaving an uncut medial web portion. Medial web portion would then be formed into a medial tube portion (like 16 in FIG. 3), e.g., by forming it around a mandrel, with or without bonding of the resulting seam. The structure would then be substantially as shown in FIG. 3 and could be further processed and used to produce a connector or plug as described above in connection with any of the subsequent FIGS. Similar web rather than tube starting structures could be used for embodiments of the type shown in FIGS. 27 and 28.

The invention claimed is:

1. The method of making a medical graft connector comprising:
   providing a metal tube;
   substantially axially cutting an axial end portion of the tube at a plurality of locations spaced circumferentially around the axial end portion to convert the axial end portion to a plurality of fingers that extend substantially axially from an adjacent end of another axial portion of the tube;
   deflecting the fingers substantially radially out from the other axial portion; and
   setting the fingers as deflected in the deflecting.

2. The method defined in claim 1 wherein the setting comprises:
   heat treating the fingers.

3. The method of making a medical graft assembly comprising:
   making a medical graft connector by the method defined in claim 1; and
   substantially coaxially attaching the medical graft connector to a tubular graft conduit.

4. The method of making an assembly for installing a medical graft comprising:
   making a medical graft assembly by the method defined in claim 3; and
   substantially coaxially surrounding the medical graft assembly with a delivery structure which elastically deflects the fingers inwardly toward parallelism with a central longitudinal axis of the other axial portion.

5. The method of installing a medical graft comprising:
   providing an assembly for installing a medical graft by the method defined in claim 4;
   inserting the delivery structure through an aperture in a side wall of a patient's tubular body conduit; and
   shifting the delivery structure relative to the medical graft assembly and the tubular body conduit so that the delivery structure is removed from the aperture but the medical graft connector is left extending through the aperture with the fingers again extending substantially radially out from the other axial portion inside the tubular body conduit.

6. The method defined in claim 1 further comprising:
   substantially axially cutting a second axial end portion of the tube remote from the axial end portion at a second plurality of locations spaced circumferentially around the second axial end portion to convert the second axial end portion to a second plurality of second fingers that extend substantially axially from an adjacent second end of the other axial portion of the tube;
   deflecting the second fingers substantially radially out from the other axial portion; and
   setting the second fingers as deflected in the deflecting of the second fingers.

7. The method defined in claim 1 further comprising:
   perforating the other axial portion.

8. The method defined in claim 1 further comprising:
   pointing free ends of the fingers.

9. The method defined in claim 1 further comprising:
   barbing free end portions of the fingers.

10. The method defined in claim 1 wherein the deflecting comprises:
    concave curving the fingers as viewed from a plane extending radially out from the other axial portion.

11. The method defined in claim 1 wherein the tube is provided with a substantially round cross section.

12. The method defined in claim 1 wherein the tube is provided with a substantially elliptical cross section.

13. The method defined in claim 6 wherein the deflecting of the fingers and the deflecting of the second fingers cause free end portions of the fingers to overlap with free end portions of the second fingers.

14. The method defined in claim 1 wherein the tube is provided with different wall thickness at different locations along its length.

15. The method defined in claim 1 wherein the cutting causes each finger to have different width at different locations along its length.

16. The method defined in claim 1 wherein the tube is provided with an axial end which is transverse but not perpendicular to a longitudinal axis of the tube.

17. The method defined in claim 1 further comprising:
    providing structure on free end portions of the fingers configured to facilitate releasable retention of the fingers in a condition in which they extend substantially parallel to a longitudinal axis of the other axial portion.

18. The method of making an assembly for installing a medical graft comprising:

making a medical graft assembly by the method defined in claim 3; and placing a removable structure around the fingers to releasably retain the fingers in a condition in which they extend substantially parallel to a longitudinal axis of the other axial portion.

19. The method of installing a medical graft comprising:

providing an assembly for installing a medical graft by the method defined in claim 18;

inserting the assembly for installing a medical graft part way through an aperture in a side wall of a patient's tubular body conduit so that the fingers are inside the tubular body conduit; and removing the structure from around the fingers so that the fingers can again extend radially out from the other axial portion inside the tubular body conduit.

20. The method defined in claim 1 further comprising:

providing an elastic web between adjacent ones of the fingers.

21. The method defined in claim 1 further comprising:

providing a second tube of an elastic material;

substantially axially cutting an axial end portion of the second tube at a second plurality of locations spaced circumferentially around the axial end portion of the second tube to convert that axial end portion to a second plurality of second fingers that extend substantially axially from an adjacent end of a second other axial portion of the second tube;

deflecting the second fingers substantially radially out from the second other axial portion;

setting the second fingers as deflected in the deflecting of the second fingers; and assembling the other axial portion substantially concentrically inside an axial end section of a tubular graft conduit and the second other axial portion substantially concentrically outside the axial end section.

22. The method defined in claim 21 wherein the assembling is performed so that the fingers extend out of the axial end section and so that the second fingers extend in a direction which is generally away from the fingers extending out of the axial end section.

23. The method defined in claim 21 wherein the assembling comprises:

securing the other axial portion and the second other axial portion relative to one another via the axial end section.

24. The method defined in claim 23 wherein the securing comprises:

suturing the other axial portion and the second other axial portion to one another through the axial end section.

25. The method of making a medical plug comprising:

providing a metal tube;

substantially axially cutting an axial end portion of the tube at a plurality of locations spaced circumferentially around the axial end portion to convert the axial end portion to a plurality of fingers that extend substantially axially from an adjacent end of another axial portion of the tube;

deflecting the fingers substantially radially out from the other axial portion;

setting the fingers as deflected in the deflecting; and occluding the other axial portion.

26. The method defined in claim 25 wherein the setting comprises:

heat treating the fingers.

27. The method of making an assembly for installing a medical plug comprising:

making a medical plug by the method defined in claim 25; and substantially coaxially surrounding the medical plug with a delivery structure which elastically deflects the fingers inwardly toward parallelism with a central longitudinal axis of the other axial portion.

28. The method of installing a medical plug comprising:

providing an assembly for installing a medical plug by the method defined in claim 27;

inserting the delivery structure through an aperture in a patient's body tissue; and shifting the delivery structure relative to the medical plug and the body tissue so that the delivery structure is removed from the aperture but the medical plug is left extending through the aperture with the fingers extending substantially radially out from the other axial portion on one side of the body tissue.

29. The method defined in claim 25 further comprising:

substantially axially cutting a second axial end portion of the tube at a second plurality of locations spaced circumferentially around the second axial end portion to convert the second axial end portion to a second plurality of second fingers that extend substantially axially from an adjacent end of the other axial portion;

deflecting the second fingers substantially radially out from the other axial portion; and setting the second fingers as deflected in the deflecting of the second fingers.

30. The method of making an assembly for installing a medical plug comprising:

making a medical plug by the method defined in claim 29; and substantially coaxially surrounding the medical plug with a delivery structure which elastically deflects the fingers and the second fingers inwardly toward parallelism with a central longitudinal axis of the other axial portion.

31. The method of installing a medical plug comprising:

providing an assembly for installing a medical plug by the method defined in claim 30;

inserting the delivery structure through an aperture in a patient's body tissue; and shifting the delivery structure relative to the medical plug and the body tissue so that the delivery structure is removed from the aperture but the medical plug is left extending through the aperture with the fingers again extending radially out from the other axial portion on one side of the body tissue and the second fingers again extending radially out from the other axial portion on an opposite side of the body tissue.

32. The method defined in claim 25 further comprising:

pointing free ends of the fingers.

33. The method defined in claim 25 further comprising:

barbing free end portions of the fingers.

34. The method defined in claim 25 wherein the deflecting comprises:

concave curving the fingers as viewed from a plane extending radially out from the other axial portion.

35. The method defined in claim 25 wherein the tube is provided with a substantially round cross section.

36. The method defined in claim 25 wherein the tube is provided with a substantially elliptical cross section.

37. The method defined in claim 29 wherein the deflecting causes free end portions of the fingers to overlap with free end portions of the second fingers.

38. The method defined in claim 25 wherein the tube is provided with different wall thickness at different locations along its length.

39. The method defined in claim 25 wherein the cutting causes each finger to have different width at different locations along its length.

40. The method defined in claim 25 further comprising:

providing structure on free end portions of the fingers configured to facilitate releasable retention of the fingers in a condition in which they extend substantially parallel to a longitudinal axis of the other axial portion.

41. The method of making an assembly for installing a medical plug comprising:

making a medical plug by the method defined in claim 25; and placing a removable structure around the fingers to releasably retain the fingers in a condition in which they extend substantially parallel to a longitudinal axis of the other axial portion.

42. The method of installing a medical plug comprising:

providing an assembly for installing a medical plug by the method defined in claim 41;

inserting the assembly for installing a medical plug part way through an aperture in a patient's body tissue so that the fingers extending from one end of the other axial portion pass through the aperture; and removing the structure from around the fingers that extend from said one end of the other axial portion so that those fingers can again extend radially out from the other axial portion and engage tissue around the aperture.

43. The method defined in claim 25 further comprising:

providing an elastic web between adjacent ones of the fingers.

* * * * *